(12) United States Patent
Biggadike et al.

(10) Patent No.: US 7,638,508 B2
(45) Date of Patent: *Dec. 29, 2009

(54) GLUCOCORTICOSTEROID COMPOUND HAVING ANTI-INFLAMMATORY ACTIVITY

(75) Inventors: Keith Biggadike, Stevenage (GB); Deborah Needham, Stevenage (GB)

(73) Assignee: Glaxo Group Limited, Greenford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 11/863,390

(22) Filed: Sep. 28, 2007

(65) Prior Publication Data

US 2008/0070880 A1  Mar. 20, 2008

Related U.S. Application Data

(63) Continuation of application No. 10/564,325, filed as application No. PCT/EP2004/007819 on Jul. 9, 2004, now Pat. No. 7,288,536.

(30) Foreign Application Priority Data

Jul. 11, 2003  (GB) .................................. 0316290.6

(51) Int. Cl.
A61K 31/56 (2006.01)
C07J 3/00 (2006.01)
(52) U.S. Cl. ...................... 514/179; 514/171; 514/180; 552/610
(58) Field of Classification Search .................. 514/179, 514/180, 171; 552/610
See application file for complete search history.

(56) References Cited

U.S. PATENT DOCUMENTS

| | | | |
|---|---|---|---|
| 3,856,828 | A | 12/1974 | Phillipps et al. |
| 4,996,335 | A | 2/1991 | Bodor et al. |
| 5,552,438 | A | 9/1996 | Christensen, IV |
| 6,172,054 | B1 | 1/2001 | Clark |
| 6,245,804 | B1 | 6/2001 | Lehmann et al. |
| 6,395,738 | B1 | 5/2002 | Ohshima et al. |
| 6,897,224 | B2 | 5/2005 | Jaroch et al. |
| 7,288,536 | B2 | 10/2007 | Biggadike et al. |
| 7,291,609 | B2 | 11/2007 | Biggadike et al. |

FOREIGN PATENT DOCUMENTS

| | | |
|---|---|---|
| GB | 1384372 | 2/1975 |
| GB | 1384732 | 2/1975 |
| GB | 1514476 | 6/1978 |
| GB | 2079755 | 1/1982 |
| GB | 2137206 | 10/1984 |
| WO | 8903390 | 4/1989 |
| WO | 9313055 | 7/1993 |
| WO | 9534534 | 12/1995 |
| WO | 9741867 | 11/1997 |
| WO | 9830537 | 7/1998 |
| WO | 9854159 | 12/1998 |
| WO | 9916766 | 4/1999 |
| WO | 9932127 | 7/1999 |
| WO | 9947505 | 9/1999 |
| WO | 9962875 | 12/1999 |
| WO | 0066590 | 11/2000 |
| WO | 0104118 | 1/2001 |
| WO | 0110143 | 2/2001 |
| WO | 0116128 | 3/2001 |
| WO | 0142193 | 6/2001 |
| WO | 0200679 | 1/2002 |
| WO | 0202565 | 1/2002 |

(Continued)

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

(Continued)

Primary Examiner—Barbara P Badio
(74) Attorney, Agent, or Firm—James P. Riek

(57) ABSTRACT

A compound of formula (I):

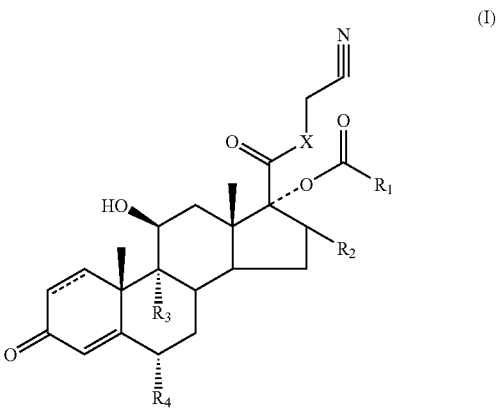

wherein
X represents O or S;
$R_1$ represents $C_{1-6}$ alkyl, $C_{3-8}$ cycloalkyl, $C_{3-8}$ cycloalkylmethyl or $C_{3-8}$ cycloalkenyl any of which optionally may be substituted by one or more methyl groups or halogen atoms or $R_1$ represents aryl, substituted aryl, heteroaryl or substituted heteroaryl;
$R_2$ represents hydrogen, methyl, which may be in either the α or β configuration, or methylene;
$R_3$ and $R_4$ are the same or different and each independently represents hydrogen, halogen or a methyl group;
and ==== represents a single or a double bond;
or a physiologically acceptable salt or solvate thereof, and pharmaceutical formulations and methods of use thereof.

25 Claims, No Drawings

FOREIGN PATENT DOCUMENTS

| | | |
|---|---|---|
| WO | 0226722 | 4/2002 |
| WO | 0240030 | 5/2002 |
| WO | 0250021 | 6/2002 |
| WO | 02066422 | 8/2002 |
| WO | 02070490 | 9/2002 |
| WO | 02076933 | 10/2002 |
| WO | 03008277 | 1/2003 |
| WO | 03024439 | 3/2003 |
| WO | 03042160 | 5/2003 |
| WO | 03059899 | 7/2003 |
| WO | 03061651 | 7/2003 |
| WO | 03072539 | 9/2003 |
| WO | 03082280 | 10/2003 |
| WO | 03082787 A1 | 10/2003 |
| WO | 03082827 | 10/2003 |
| WO | 03086294 | 10/2003 |
| WO | 03091204 | 11/2003 |
| WO | 03101932 A2 | 12/2003 |
| WO | 03104195 | 12/2003 |
| WO | 2004005229 | 1/2004 |
| WO | 2004009016 | 1/2004 |
| WO | 2004009017 | 1/2004 |
| WO | 2004016578 | 2/2004 |
| WO | 2004018429 | 3/2004 |
| WO | 2004022547 | 3/2004 |
| WO | 2004024728 | 3/2004 |
| WO | 2004026248 | 4/2004 |
| WO | 2004037768 A2 | 5/2004 |
| WO | 2004037773 | 5/2004 |
| WO | 2004037807 | 5/2004 |
| WO | 2004039762 | 5/2004 |
| WO | 2004039766 | 5/2004 |
| WO | 2004056823 A2 | 7/2004 |
| WO | 2004103998 A1 | 12/2004 |
| WO | 2005005451 A1 | 1/2005 |

OTHER PUBLICATIONS

Vippagunta et al. (Advanced Drug Delivery Reviews, 48 (2001), pp. 3-26).*

Szelenyi et al.; "Loteprednol Etabonate: a Soft Steroid for the Treatment of Allergic Diseases of the Airways"; Drugs of Today; 2000; vol. 36, No. 5; pp. 313-320.

Ueno et al.; "Synthesis and Evaluation of Anti-inflammatory Activities of a Series of Corticosteroid 17a-Esters Containing a Functional Group"; Journal of Medicinal Chemistry; 1991; vol. 34, No. 8; pp. 2468-2473.

Austin et al.; "Mometasone Furoate is a Less Specific Glucocorticoid than Fluticasone Propionate"; Eur. Resp. J.; 2002; vol. 20, No. 6; pp. 1386-1392.

Fujii et al.; "Novel Phosphodiesterase 4 Inhibitor T-440 Reverses and Prevents Human Bronchial Contraction Induced by Allergen"; J. Pharmacol. Exp. Ther.; 1998; vol. 284, No. 1; p. 162-169.

Landells et al.; "Oral Administration of the Phosphodiesterase (PDE)4 Inhibitor, V11294A Inhibits Ex-Vivo Agonist-Induced Cell Activation" (Annu Cong Eur Resp Soc, Sep. 22, 1998); Eur. Resp. J.; 1998; vol. 12, Suppl. 28; Abstract P2393, p. 362s.

Phillipps et al.; "Synthesis and Structure-Activity Relationships in a Series of Anti-inflammatory Corticosteroid Analogues, Halomethyl Androstane-17B-carbothioates and -17B-carboselenoates"; J. Med. Chem.; 1994; vol. 37, No. 22; pp. 3717-3729.

Rachwal et al.; "Chemistry of Ioteprednol etabonate and related steroids. II. Reactions at ring C and NMR structural studies of the resulting compounds"; Steroids; 1998; vol. 63, No. 4; p. 193-201.

Ray et al.; "Induction of the E-Selectin Promoter by Interleukin 1 and Tumor Necrosis Factor x, and Inhibition by Glucocorticoids"; Biochem. J.; 1997; vol. 328; pp. 707-715.

Druzgala et al.; "Soft Drugs—10. Blanching Activity and Receptor Binding Affinity of a New Type of Glucocorticoid: Loteprednol Etabonate"; J. Steroid Biochem. Molec. Biol.; 1991; vol. 38, No. 2; pp. 149-154.

* cited by examiner

GLUCOCORTICOSTEROID COMPOUND HAVING ANTI-INFLAMMATORY ACTIVITY

This application is a Continuation application of U.S. patent application Ser. No. 10/564,325, filed 17 May 2006, now U.S. Pat. No. 7,288,536, which was a 35 U.S.C. 371 United States National Phase Application of International Application No. PCT/EP2004/007819 filed 9 Jul. 2004, which claims priority from GB 0316290.6 filed 11 Jul. 2003.

The present invention relates to compounds which are glucocorticoid receptor agonists of the androstane series and to processes for their preparation. The present invention also relates to pharmaceutical formulations containing the compounds and to therapeutic uses thereof, particularly for the treatment of inflammatory and allergic conditions.

Glucocorticosteroids which have anti-inflammatory properties are known and are widely used for the treatment of inflammatory disorders or diseases such as asthma and rhinitis. However, we have identified a novel series of glucocorticosteroids.

Thus, according to one aspect of the invention, there is provided a compound of formula (I)

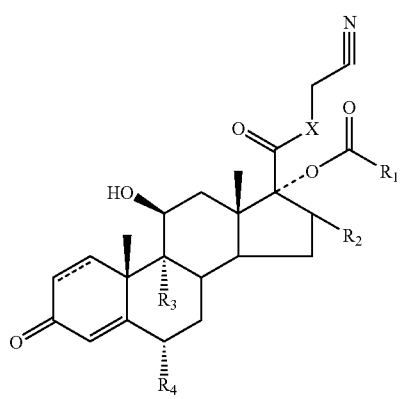

wherein

X represents O or S;

$R_1$ represents $C_{1-6}$ alkyl, $C_{3-8}$ cycloalkyl, $C_{3-8}$ cycloalkylmethyl or $C_{3-8}$ cycloalkenyl any of which optionally may be substituted by one or more methyl groups or halogen atoms or $R_1$ represents aryl, substituted aryl, heteroaryl or substituted heteroaryl;

$R_2$ represents hydrogen, methyl, which may be in either the α or β configuration, or methylene;

$R_3$ and $R_4$ are the same or different and each independently represents hydrogen, halogen or a methyl group;

and ----- represents a single or a double bond;

or a physiologically acceptable salt or solvate thereof.

Examples of solvates include hydrates.

References hereinafter to a compound according to the invention includes both compounds of formula (I) and salts and solvates thereof.

It will be appreciated that the invention includes within its scope all stereoisomers of the compounds of formula (I) and mixtures thereof.

Preferably, the absolute stereochemistry will be as shown in the representation of compounds of formula (I).

Preferably, X represents O.

Preferred examples of $C_{1-6}$ alkyl groups that $R_1$ may represent include 2,2-dimethyl propyl.

Preferred examples of $C_{3-8}$ cycloalkyl groups that $R_1$ may represent include cyclopropyl, cyclobutyl, cyclopentyl and cyclohexyl and substituted derivatives such as methylcyclopropyl (eg 1-methylcyclopropyl), dichlorodimethylcyclopropyl (eg 2,2-dichloro-3,3-dimethylcyclopropyl) and tetramethylcyclopropyl (eg 2,2,3,3-tetramethylcyclopropyl).

Preferred examples of $C_{3-8}$ cycloalkylmethyl groups that $R_1$ may represent include cyclopentylmethyl.

Preferred examples of $C_{3-8}$ cycloalkenyl groups that $R_1$ may represent include alkenyl groups containing 1 or more double bonds (not being aromatic groups) such as cyclohexenyl eg cyclohex-2,3-enyl.

In some embodiments it is preferred that $R_1$ represents a substituted aryl group.

Preferred examples of substituted aryl groups that $R_1$ may represent include 4-(diethylamino)sulphonylphenyl, 2,6-difluorophenyl, 4-methoxyphenyl, 3-difluoromethylthiophenyl and 4-cyanophenyl.

Preferred examples of heteroaryl groups that $R_1$ may represent include quinoline-2-yl.

Preferred examples of substituted heteroaryl groups that $R_1$ may represent include 5-chloro-4-methoxy-thiophene-3-yl, 2-isopropyl-1,3-thiazol-4-yl, 5-trifluoromethylfuran-2-yl, 5-methylsulphonyl-thiophene-2-yl, 5-methylthio-thiophene-2-yl and 5-ethyl-isoxazol-3-yl.

We prefer $R_1$ to represent $C_{3-8}$ cycloalkyl optionally substituted by one or more methyl and/or halogen groups. We particularly prefer $R_1$ to represent $C_{3-6}$ cycloalkyl optionally substituted by one or more methyl or chlorine groups.

Most preferred groups that $R_1$ may represent include tetramethylcyclopropyl, dichlorodimethylcyclopropyl, cyclohexyl, and cyclopentylmethyl, especially 2,2,3,3-tetramethylcyclopropyl and 2,2-dichloro-3,3-dimethylcyclopropyl, most especially 2,2,3,3-tetramethylcyclopropyl.

We prefer $R_2$ to represent methyl, especially methyl in the α configuration.

Compounds of formula (I) in which $R_3$ and $R_4$, which can be the same or different, each represents hydrogen, methyl, fluorine or chlorine, particularly hydrogen or fluorine are preferred. Especially preferred are compounds in which $R_3$ and $R_4$ are both fluorine.

Preferably, ----- represents a double bond.

It is to be understood that the present invention covers all combinations of particularly and preferred groups referred to hereinabove.

Preferred compounds of formula (I) include:
6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester;
17α-(4-[(Diethylamino)sulphonyl]benzoyl)oxy-6α,9α-difluoro-11β-hydroxy-16α-methyl-3-oxo-androsta-1,4-diene-17β-carbothioic acid S-cyanomethyl ester;
17α-(5-Chloro-4-methoxy-thiophene-3-carbonyl)oxy-6α,9α-difluoro-11β-hydroxy-16α-methyl-3-oxo-androsta-1,4-diene-17β-carbothioic acid S-cyanomethyl ester;
6α,9α-Difluoro-11β-hydroxy-16α-methyl-3-oxo-17α-(2,2,3,3-tetramethycyclopropylcarbonyl)oxy-androsta-1,4-diene-17β-carboxylic acid cyanomethyl ester;
17α-(Cyclohexylcarbonyl)oxy-6α,9α-difluoro-11β-hydroxy-16α-methyl-3-oxo-androsta-1,4-diene-17β-carboxylic acid cyanomethyl ester;

6α,9α-Difluoro-17α-(2,6-difluorobenzoyl)oxy-11β-hydroxy-16α-methyl-3-oxo-androsta-1,4-diene-17β-carboxylic acid cyanomethyl ester;
6α,9α-Difluoro-11β-hydroxy-17α-(4-methoxybenzoyl)oxy-16α-methyl-3-oxo-androsta-1,4-diene-17β-carboxylic acid cyanomethyl ester;
17α-(4-Cyanobenzoyl)oxy-6α,9α-difluoro-11β-hydroxy-16α-methyl-3-oxo-androsta-1,4-diene-17β-carboxylic acid cyanomethyl ester;
17α-(Cyclopentylmethylcarbonyl)oxy-6α,9-difluoro-11β-hydroxy-16α-methyl-3-oxo-androsta-1,4-diene-17β-carboxylic acid cyanomethyl ester;
6α,9α-Difluoro-17α-(3,3-dimethylbutanoyl)oxy-11β-hydroxy-16α-methyl-3-oxo-androsta-1,4-diene-17β-carboxylic acid cyanomethyl ester;
6α,9α-Difluoro-11β-hydroxy-17α-(2-isopropyl-1,3-thiazole-4-carbonyl)oxy-16α-methyl-3-oxo-androsta-1,4-diene-17β-carboxylic acid cyanomethyl ester;
6α,9α-Difluoro-11β-hydroxy-16α-methyl-3-oxo-17α-(quinoline-2-carbonyl)oxy-androsta-1,4-diene-17β-carboxylic acid cyanomethyl ester;
6α,9α-Difluoro-11β-hydroxy-16α-methyl-3-oxo-17α-(5-trifluoromethyl-furan-2-carbonyl)oxy-androsta-1,4-diene-17β-carboxylic acid cyanomethyl ester;
6α,9α-Difluoro-11β-hydroxy-16α-methyl-17α-(5-methylsulphonyl-thiophene-2-carbonyl)oxy-3-oxo-androsta-1,4-diene-17β-carboxylic acid cyanomethyl ester;
6α,9α-Difluoro-11β-hydroxy-16α-methyl-17α-(5-methylthio-thiophene-2-carbonyl)oxy-3-oxo-androsta-1,4-diene-17β-carboxylic acid cyanomethyl ester;
6α,9α-Difluoro-17α-(5-ethyl-isoxazole-3-carbonyl)oxy-11β-hydroxy-16α-methyl-3-oxo-androsta-1,4-diene-17β-carboxylic acid cyanomethyl ester;
9α-Fluoro-11β-hydroxy-16β-methyl-3-oxo-17α-(2,2,3,3-tetramethylcyclopropylcarbonyl)oxy-androsta-1,4-diene-17β-carboxylic acid cyanomethyl ester.
6α,9α-Difluoro-11β-hydroxy-16α-methyl-3-oxo-17α-(2,2,3,3-tetramethycyclopropylcarbonyl)oxy-androst-4-ene-17β-carboxylic acid cyanomethyl ester;
17α-(5-Chloro-4-methoxy-thiophene-3-carbonyl)oxy-6α,9α-difluoro-11β-hydroxy-16α-methyl-3-oxo-androsta-1,4-diene-17β-carboxylic acid cyanomethyl ester;
17α-(2,2-Dichloro-3,3-dimethylclopropylcarbonyl)oxy-6α,9α-difluoro-11β-hydroxy-16α-methyl-3-oxo-androsta-1,4-diene-17β-carboxylic acid cyanomethyl ester;
17α-(2,2-Dichloro-3,3-dimethylclopropylcarbonyl)oxy-6α,9α-difluoro-11β-hydroxy-16α-methyl-3-oxo-androsta-1,4-diene-17β-carbothioic acid S-cyanomethyl ester;
17α-(Cyclohexylcarbonyl)oxy-6α,9α-difluoro-11β-hydroxy-16α-methyl-3-oxo-androsta-1,4-diene-17β-carbothioic acid S-cyanomethyl ester;
6α,9α-Difluoro-11β-hydroxy-16α-methyl-17α-(5-methylsulphonyl-thiophene-2-carbonyl)oxy-3-oxo-androsta-1,4-diene-17β-carbothioic acid S-cyanomethyl ester;
6α,9α-Difluoro-11β-hydroxy-16α-methyl-3-oxo-17α-(5-trifluoromethyl-furan-2-carbonyl)oxy-androsta-1,4-diene-17β-carbothioic acid S-cyanomethyl ester; and
6α,9α-Difluoro-17α-(3-(difluoromethylthio)benzoyl)oxy-11β-hydroxy-16α-methyl-3-oxo-androsta-1,4-diene-17β-carbothioic acid S-cyanomethyl ester;
Particularly preferred compounds are:
6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester;
6α,9α-Difluoro-11β-hydroxy-16α-methyl-3-oxo-17α-(2,2,3,3-tetramethycyclopropylcarbonyl)oxy-androsta-1,4-diene-17β-carboxylic acid cyanomethyl ester;
9α-Fluoro-11β-hydroxy-16β-methyl-3-oxo-17α-(2,2,3,3-tetramethylcyclopropylcarbonyl)oxy-androsta-1,4-diene-17β-carboxylic acid cyanomethyl ester;
17α-(Cyclohexylcarbonyl)oxy-6α,9α-difluoro-11β-hydroxy-16α-methyl-3-oxo-androsta-1,4-diene-17β-carboxylic acid cyanomethyl ester;
17α-(Cyclopentylmethylcarbonyl)oxy-6α,9α-difluoro-11β-hydroxy-16α-methyl-3-oxo-androsta-1,4-diene-17β-carboxylic acid cyanomethyl ester;
6α,9α-Difluoro-17α-(3,3-dimethylbutanoyl)oxy-11β-hydroxy-16α-methyl-3-oxo-androsta-1,4-diene-17β-carboxylic acid cyanomethyl ester;
6α,9α-Difluoro-17α-(3-(difluoromethylthio)benzoyl)oxy-11β-hydroxy-16α-methyl-3-oxo-androsta-1,4-diene-17β-carbothioic acid S-cyanomethyl ester;
17α-(Cyclohexylcarbonyl)oxy-6α,9α-difluoro-11β-hydroxy-16α-methyl-3-oxo-androsta-1,4-diene-17β-carbothioic acid S-cyanomethyl ester;
6α,9α-Difluoro-17α-(5-ethyl-isoxazole-3-carbonyl)oxy-11β-hydroxy-16α-methyl-3-oxo-androsta-1,4-diene-17β-carboxylic acid cyanomethyl ester;
6α,9α-Difluoro-11β-hydroxy-16α-methyl-17α-(5-methylthio-thiophene-2-carbonyl)oxy-3-oxo-androsta-1,4-diene-17β-carboxylic acid cyanomethyl ester;
6α,9α-Difluoro-11β-hydroxy-17α-(2-isopropyl-1,3-thiazole-4-carbonyl)oxy-16α-methyl-3-oxo-androsta-1,4-diene-17β-carboxylic acid cyanomethyl ester;
17α-(2,2-Dichloro-3,3-dimethylclopropylcarbonyl)oxy-6α, 9α-difluoro-11β-hydroxy-16α-methyl-3-oxo-androsta-1,4-diene-17β-carbothioic acid S-cyanomethyl ester; and
17α-(2,2-Dichloro-3,3-dimethylclopropylcarbonyl)oxy-6α, 9α-difluoro-11β-hydroxy-16α-methyl-3-oxo-androsta-1,4-diene-17β-carboxylic acid cyanomethyl ester;

especially preferred are
17α-(2,2-Dichloro-3,3-dimethylclopropylcarbonyl)oxy-6α,9α-difluoro-11β-hydroxy-16α-methyl-3-oxo-androsta-1,4-diene-17β-carboxylic acid cyanomethyl ester;
6α,9α-Difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester; and
6α,9α-Difluoro-11β-hydroxy-16α-methyl-3-oxo-17α-(2,2,3,3-tetramethycyclopropylcarbonyl)oxy-androsta-1,4-diene-17β-carboxylic acid cyanomethyl ester Most preferred is
6α,9α-Difluoro-11β-hydroxy-16α-methyl-3-oxo-17α-(2,2,3,3-tetramethycyclopropylcarbonyl)oxy-androsta-1,4-diene-17β-carboxylic acid cyanomethyl ester.

The compounds of formula (I) have potentially beneficial anti-inflammatory or anti-allergic effects, particularly upon topical administration, demonstrated by, for example, their ability to bind to the glucocorticoid receptor and to illicit a response via that receptor. Hence, the compounds of formula (I) are potentially useful in the treatment of inflammatory and/or allergic disorders.

Examples of disease states in which the compounds of the invention may have utility include skin diseases such as eczema, psoriasis, allergic dermatitis neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

Compounds of the invention may also have use in the treatment of conjunctiva and conjunctivitis.

It will be appreciated by those skilled in the art that reference herein to treatment extends to prophylaxis as well as the treatment of established conditions.

As mentioned above, compounds of formula (I) may be useful in human or veterinary medicine, in particular as anti-inflammatory and anti-allergic agents.

There is thus provided as a further aspect of the invention a compound of formula (I) or a physiologically acceptable solvate thereof for use in human or veterinary medicine, particularly in the treatment of patients with inflammatory and/or allergic conditions.

According to another aspect of the invention, there is provided the use of a compound of formula (I) or a physiologically acceptable solvate thereof for the manufacture of a medicament for the treatment of patients with inflammatory and/or allergic conditions.

In a further or alternative aspect, there is provided a method for the treatment of a human or animal subject with an inflammatory and/or allergic condition, which method comprises administering to said human or animal subject an effective amount of a compound of formula (I) or physiologically acceptable solvate thereof.

The compounds according to the invention may be formulated for administration in any convenient way, and the invention therefore also includes within its scope pharmaceutical compositions comprising a compound of formula (I) or physiologically acceptable solvate thereof together, if desirable, in admixture with one or more physiologically acceptable diluents or carriers.

Further, there is provided a process for the preparation of such pharmaceutical compositions which comprises mixing the ingredients.

The compounds according to the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol.

Advantageously, the formulations of the invention may be buffered by the addition of suitable buffering agents.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain between 20 μg-10 mg of the compound of formula (I). Alternatively, the compound of the invention may be presented without excipients such as lactose.

The proportion of the active compound of formula (I) in the local compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will be within the range of from 0.1 to 5%.

Aerosol formulations are preferably arranged so that each metered dose or "puff" of aerosol contains 20 μg-2000 μg, preferably about 20 μg-500 μg of a compound of formula (I). Administration may be once daily or several times daily, for example 2, 3, 4 or 8 times, giving for example 1, 2 or 3 doses each time. The overall daily dose with an aerosol will be within the range 100 μg-10 mg preferably, 200 μg-2000 μg. The overall daily dose and the metered dose delivered by capsules and cartridges in an inhaler or insufflator will generally be double those with aerosol formulations.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the compounds of the invention.

The compounds according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example another corticosteroid or an NSAID), an anticholinergic agent, a $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a $\beta_2$-adrenoreceptor agonist, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

A combination comprising of compound of the invention together with a $\beta_2$-adrenoreceptor agonist is particularly preferred.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period such as salmeterol or formoterol.

Preferred long acting $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Especially preferred long-acting $\beta_2$-adrenoreceptor agonists include compounds of formula (XX):

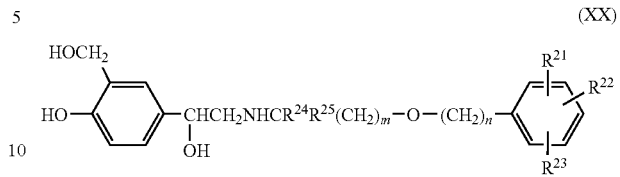

or a salt or solvate thereof, wherein:

m is an integer of from 2 to 8;

n is an integer of from 3 to 11, with the proviso that m+n is 5 to 19, $R^{21}$ is $-XSO_2NR^{26}R^{27}$ wherein X is $-(CH_2)_p-$ or $C_{2-6}$ alkenylene;

$R^{26}$ and $R^{27}$ are independently selected from hydrogen, $C_{1-6}$alkyl, $C_{3-7}$cycloalkyl, $C(O)NR^{28}R^{29}$, phenyl, and phenyl $(C_{1-4}$alkyl)-, or $R^{26}$ and $R^{27}$, together with the nitrogen to which they are bonded, form a 5-, 6-, or 7-membered nitrogen containing ring, and $R^{26}$ and $R^{27}$ are each optionally substituted by one or two groups selected from halo, $C_{1-6}$alkyl, $C_{1-6}$haloalkyl, $C_{1-6}$alkoxy, hydroxy-substituted $C_{1-6}$alkoxy, $-CO_2R^{28}$, $-SO_2NR^{28}R^{29}$, $-CONR^{28}R^{29}$, $-NR^{28}C(O)R^{29}$, or a 5-, 6- or 7-membered heterocylic ring;

$R^{28}$ and $R^{29}$ are independently selected from hydrogen, $C_{1-6}$alkyl, $C_{3-6}$cycloalkyl, phenyl, and phenyl$(C_{1-4}$alkyl)-; and p is an integer of from 0 to 6, preferably from 0 to 4;

$R^{22}$ and $R^{23}$ are independently selected from hydrogen, $C_{1-6}$alkyl, $C_{1-6}$alkoxy, halo, phenyl, and $C_{1-6}$haloalkyl; and $R^{24}$ and $R^{25}$ are independently selected from hydrogen and $C_{1-4}$alkyl with the proviso that the total number of carbon atoms in $R^{24}$ and $R^{25}$ is not more than 4.

Especially preferred long-acting $\beta_2$-adrenoreceptor agonists are:

3-(4-{[6-({(2R)-2-hydroxy-2-[4-hydroxy-3-(hydroxymethyl)phenyl]ethyl}amino) hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl) amino]-1-hydroxyethyl}-2-(hydroxymethyl)phenol;

4-{(1R)-2-[(6-{4-[3-(cyclopentylsulfonyl)phenyl] butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]foramide, and N-2{2-[4-(3-phenyl-4-methoxyphenyl)aminophenyl]ethyl}-2-hydroxy-2-(8-hydroxy-2(1H)-quinolinon-5-yl)ethylamine.

Suitable anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (eg. the 17-propionate ester or the 17,21-dipropionate ester), budesonide, flunisolide, mometasone esters (eg. the furoate ester), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds having glucocorticoid agonism that may posess selectivity for transrepression over transactivation and that may be useful in combination therapy include those covered in the following patents: WO03/082827, WO01/10143, WO98/54159, WO04/005229, WO04/009016, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277.

Suitable anti-inflammatory agents include non-steroidal anti-inflammatory drugs (NSAID's).

Suitable NSAID's include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis (eg. montelukast), iNOS inhibitors, tryptase and elastase inhibitors, beta-2 integrin antagonists and adenosine receptor agonists or antagonists (e.g. adenosine 2a agonists), cytokine antagonists (e.g. chemokine antagonists, such as a CCR3 antagonist) or inhibitors of cytokine synthesis, or 5-lipoxygenase inhibitors. Suitable other β$_2$-adrenoreceptor agonists include salmeterol (e.g. as the xinafoate), salbutamol (e.g. as the sulphate or the free base), formoterol (e.g. as the fumarate), fenoterol or terbutaline and salts thereof. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

Of particular interest is use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds of interest are disclosed in the published international patent application WO04/024728 (Glaxo Group Ltd), PCT/EP2003/014867 (Glaxo Group Ltd) and PCT/EP2004/005494 (Glaxo Group Ltd).

Suitable anticholinergic agents are those compounds that act as antagonists at the muscarinic receptors, in particular those compounds which are antagonists of the M$_1$ or M$_3$ receptors, dual antagonists of the M$_1$/M$_3$ or M$_2$/M$_3$, receptors or pan-antagonists of the M$_1$/M$_2$/M$_3$ receptors. Exemplary compounds for administration via inhalation include ipratropium (e.g. as the bromide, CAS 22254-24-6, sold under the name Atrovent), oxitropium (e.g. as the bromide, CAS 30286-75-0) and tiotropium (e.g. as the bromide, CAS 136310-93-5, sold under the name Spiriva). Also of interest are revatropate (e.g. as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (e.g. as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other suitable anticholinergic agents include compounds of formula (XXI), which are disclosed in U.S. patent application 60/487,981:

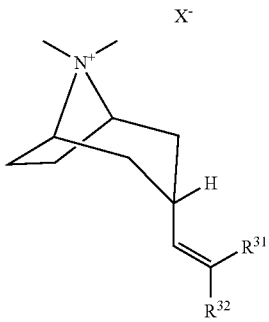

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further suitable anticholinergic agents include compounds of formula (XXII) or (XXIII), which are disclosed in U.S. patent application 60/511,009:

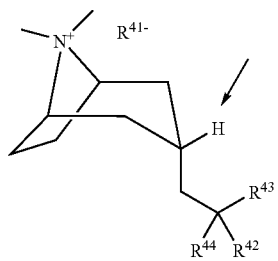

(XXII)

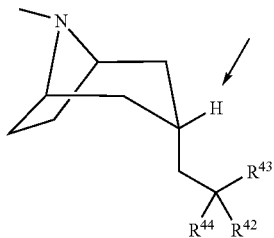

(XXIII)

wherein:

the H atom indicated is in the exo position;

$R^{41}$ represents an anion associated with the positive charge of the N atom. $R^{41}$ may be but is not limited to chloride, bromide, iodide, sulfate, benzene sulfonate and toluene sulfonate;

$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;

$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —$CN$, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CQ(R^{46})$, $CH_2N(R^{48})SO_2(R^{46})$, —$CH_2N(R^{48})CO_2(R^{45})$, —$CH_2N(R^4)CONH(R^{47})$;

$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;

$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(Endo)-3-(2-methoxy-2,2-di-thiophen-2-yl-ethyl)-8,8-dimethyl-8-azonia-bicyclo[3.2.1]octane iodide;

3-((Endo)-8-methyl-8-aza-bicyclo[3.2.1]oct-3-yl)-2,2-diphenyl-propionitrile;

(Endo)-8-methyl-3-(2,2,2-triphenyl-ethyl)-8-aza-bicyclo[3.2.1]octane;

3-((Endo)-8-methyl-8-aza-bicyclo[3.2.1]oct-3-yl)-2,2-diphenyl-propionamide;

3-((Endo)-8-methyl-8-aza-bicyclo[3.2.1]oct-3-yl)-2,2-diphenyl-propionic acid;

(Endo)-3-(2-cyano-2,2-diphenyl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane bromide;

3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8-dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

More preferred compounds useful in the present invention include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Suitable antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, e.g diphenylhydramine, pyrilamine, clemastine, chloropheniramine. Second generation antagonists, which are non-sedating, include loratidine, desloratidine, terfenadine, astemizole, acrivastine, azelastine, levocetirizine fexofenadine and cetirizine.

Examples of preferred anti-histamines include loratidine, desloratidine, fexofenadine and cetirizine.

The invention thus provides, in a further aspect, a combination comprising a compound of formula (I) a pharmaceutically acceptable salt, solvate or physiologically functional derivative thereof together with a PDE4 inhibitor.

The invention thus provides, in a further aspect, a combination comprising a compound of formula (I) a pharmaceutically acceptable salt, solvate or physiologically functional derivative thereof together with a $\beta_2$-adrenorecptor agonist.

The invention thus provides, in a further aspect, a combination comprising a compound of formula (I) a pharmaceutically acceptable salt, solvate or physiologically functional derivative thereof together with an anticholinergic.

The invention thus provides, in a further aspect, a combination comprising a compound of formula (I) a pharmaceutically acceptable salt, solvate or physiologically functional derivative thereof together with an antihistamine.

The invention thus provides, in a further aspect, a combination comprising a compound of formula (I) a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of formula (I) a pharmaceutically acceptable salt, solvate or physiologically functional derivative thereof together with an anticholinergic and a PDE-4 inhibitor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Preferably the individual compounds of such combinations may be administered simultaneously in a combined pharmaceutical combination. Appropriate doses of known therapeutic agents will be readily appreciated by those skilled in the art.

The compounds of formula (I) and solvates thereof may be prepared by the methodology described hereinafter, constituting a further aspect of this invention.

The compounds of formula (I) and solvates thereof may be prepared by the methodology described hereinafter, constituting a further aspect of this invention.

A process according to the invention for preparing a compound of formula (I) comprises reaction of a carboxylic acid (X=O) or carbothioic acid (X=S) of formula (II)

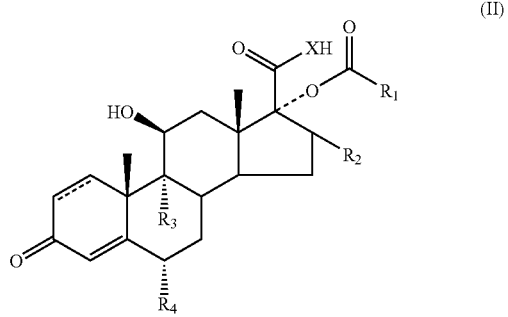

(II)

wherein $R_1$, $R_2$, $R_3$, $R_4$, X and $=\!\!=$ are as defined above, with a compound of formula L-CH$_2$—CN wherein L represents a leaving group.

In this process the compound of formula (II) may be reacted with a compound of formula L-CH$_2$—CN wherein L represents a leaving group such as halogen atom or a tosyl or mesyl group or the like, under standard conditions. For example the reaction may be performed in an inert polar organic solvent e.g. N,N-dimethylformamide in the presence of a base e.g. potassium carbonate, sodium bicarbonate.

Compounds of formula (II) may conveniently be employed as salts when such salts may be prepared in crystalline form, or as solvates.

Compounds of formula L-CH$_2$—CN are either known or may be prepared by known methods.

Compounds of formula (II) may be prepared from the corresponding 17α-hydroxyl derivative of formula (III):

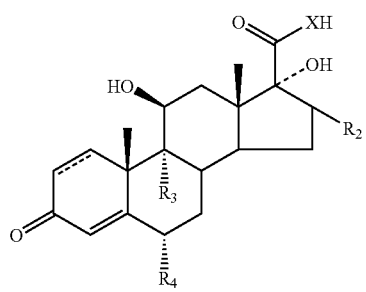

wherein R$_2$, R$_3$, R$_4$, X and ==== are as defined above, using for example, the methodology described by G. H. Phillipps et al., Journal of Medicinal Chemistry, (1994), 37, 3717-3729. The step typically comprises the addition of a reagent suitable for performing the esterification to the ester such as a compound of formula R$_1$COOH or an activated derivative thereof eg an activated ester, anhydride or halide thereof especially an acid halide eg the acid chloride in the presence of a mild base e.g. triethylamine. Imidazolium esters may offer convenient alternatives to the acid chloride in this reaction. For example the 1,2-dimethyl-1H-imidazolium ester (IV) represents a convenient crystalline activated derivative of 2,2,3,3-tetramethylcyclopropane carboxylic acid.

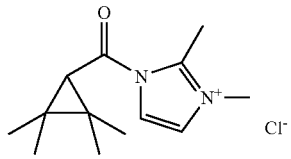

Generally the acid chloride or other activated carboxylic acid derivative would be employed in at least 2 times molar quantity relative to the compound of formula (III). The second mole of acid chloride tends to react with the carboxylic/carbothioc acid moiety in the compound of formula (III) and would need to be removed by reaction with an amine such as diethylamine or 1-methylpiperazine.

In a further aspect of the invention there is provided a process for preparing a compound of formula (II)

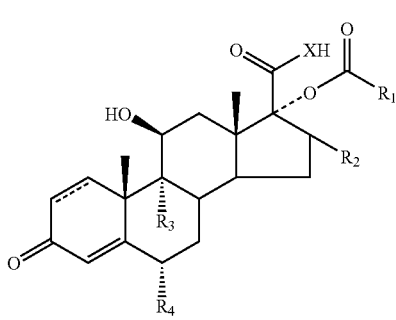

where R$_1$ represents 2,2,3,3-tetramethyl cyclopropyl and R$_2$, R$_3$, R$_4$, X and ==== are defined above, which process comprises reaction of the 1,2-dimethyl-1H-imidazolium ester of 2,2,3,3-tetramethylcyclopropane carboxylic acid (IV):

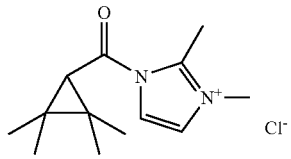

with the corresponding 17α-hydroxyl derivative of formula (III)

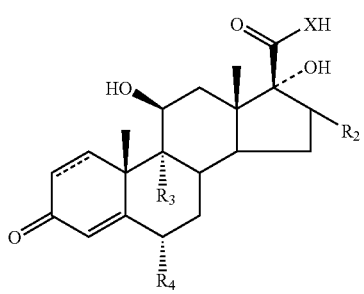

Compounds of formula (III) are either known or may be prepared in accordance with procedures described by G. H. Phillipps et al., Journal of Medicinal Chemistry, (1994), 37, 3717-3729.

The following compounds of formula (II) are new and form an aspect of the invention:

17α-(4-[(Diethylamino)sulphonyl]benzoyl)oxy-6α,9α-difluoro-11β-hydroxy-16α-methyl-3-oxo-androsta-1,4-diene-17β-carbothioic acid, 6α,9α-Difluoro-17α-(2,6-difluorobenzoyl)oxy-11β-hydroxy-16α-methyl-3-oxo-androsta-1,4-diene-17β-carboxylic acid, 6α,9α-Difluoro-11β-hydroxy-17α-(4-methoxybenzoyl)oxy-16α-methyl-3-oxo-androsta-1,4-diene-17β-carboxylic acid, 17α-(4-Cyanobenzoyl)oxy-6α,9α-difluoro-11β-hydroxy-16α-methyl-3-oxo-androsta-1,4-diene-17β-carboxylic acid, 6α,9α-Difluoro-17α-(3,3-dimethylbutanoyl)oxy-11β-hydroxy-16α-methyl-3-oxo-androsta-1,4-diene-17β-carboxylic acid, 6α,9α-Difluoro-11β-hydroxy-17α-(2-isopropyl-1,3-thiazole-4-carbonyl)oxy-16α-methyl-3-oxo-androsta-1,4-diene-17β-carboxylic acid, 6α,9α-Difluoro-11β-hydroxy-16α-methyl-3-oxo-17α-(quinoline-2-carbonyl)oxy-androsta-1,4-diene-17β-carboxylic acid, 6α,9α-Difluoro-11β-hydroxy-16α-methyl-3-oxo-17α-(5-trifluoromethyl-furan-2-carbonyl)oxy-androsta-1,4-diene-17β-carboxylic acid, 6α,9α-Difluoro-11β-hydroxy-16α-methyl-17α-(5-methylsulphonyl-thiophene-2-carbonyl)oxy-3-oxo-androsta-1,4-diene-17β-carboxylic acid, 6α,9α-Difluoro-11β-hydroxy-16α-methyl-17α-(5-methylthio-thiophene-2-carbonyl)oxy-3-oxo-androsta-1,4-diene-17β-carboxylic acid, 6α,9α-Difluoro-17α-(5-ethyl-isoxazole-3-carbonyl)oxy-11β-hydroxy-16α-methyl-3-oxo-androsta-1,4-diene-17β-carboxylic acid,
17α-(5-Chloro-4-methoxy-thiophene-3-carbonyl)oxy-6α,9α-difluoro-11β-hydroxy-16α-methyl-3-oxo-androsta-1,4-diene-17β-carboxylic acid,
17α-(2,2-Dichloro-3,3-dimethylclopropylcarbonyl)oxy-6α,9α-difluoro-11β-hydroxy-16α-methyl-3-oxo-androsta-1,4-diene-17β-carboxylic acid,
17α-(2,2-Dichloro-3,3-dimethylclopropylcarbonyl)oxy-6α,9α-difluoro-11β-hydroxy-16α-methyl-3-oxo-androsta-1,4-diene-17β-carbothioic acid,
6α,9α-Difluoro-11β-hydroxy-16α-methyl-17α-(5-methylsulphonyl-thiophene-2-carbonyl)oxy-3-oxo-androsta-1,4-diene-17β-carbothioic acid,
6α,9α-Difluoro-11β-hydroxy-16α-methyl-3-oxo-17α-(5-trifluoromethyl-furan-2-carbonyl)oxy-androsta-1,4-diene-17β-carbothioic acid, and
6α,9α-Difluoro-17α-(3-(difluoromethylthio)benzoyl)oxy-11β-hydroxy-16α-methyl-3-oxo-androsta-1,4-diene-17β-carbothioic acid.

Compound of formula (IV), 3-dimethyl-1-[(2,2,3,3-tetramethylcyclopropyl)carbonyl]-1H-imidazol-3-ium chloride is new and forms an aspect of the invention.

Compounds of formula (III) may also be prepared by a process comprising the following steps:

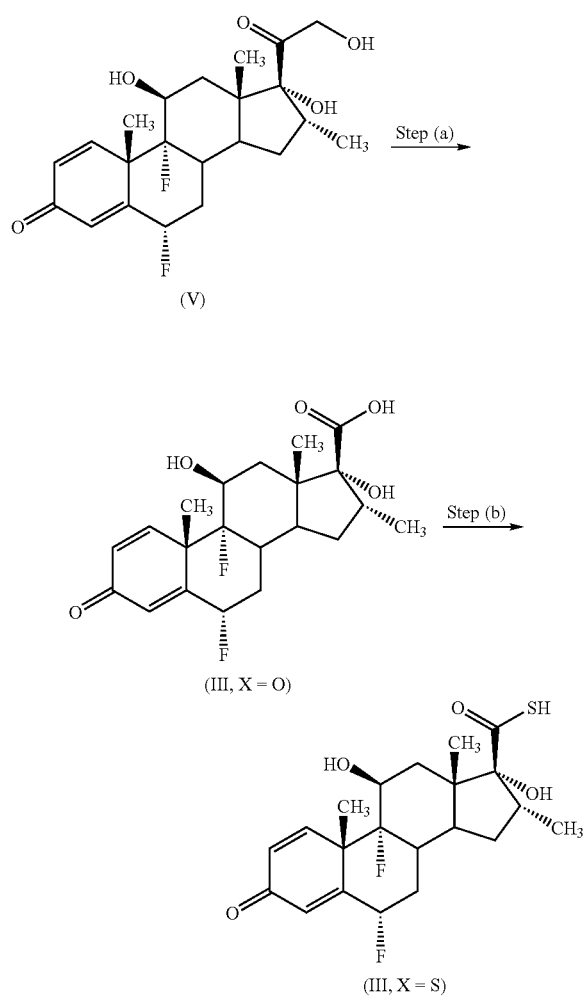

Step (a) comprises oxidation of a solution containing the compound of formula (V) to give the carboxylic acid (III, X=O);

Preferably, step (a) will be performed in the presence of a solvent comprising methanol, water, tetrahydrofuran, dioxan or diethylene glygol dimethylether. For example, so as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1-9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3 wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, eg. one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. eg for 2 hours. The compound of formula (III, X=O) may be isolated by recrystallisation from the reaction mixture by addition of an anti-solvent. A suitable anti-solvent for compound of formula (III, X=O) is water. Surprisingly we have discovered that it is highly desirable to control the conditions under which the compound of formula (III, X=O) is precipitated by addition of anti-solvent eg water. When the recrystallisation is performed using chilled water (eg water/ice mixture at a temperature of 0-5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice By contrast when conditions of around 10° C. or higher are used (eg around ambient temperature) a granular product of a sand like consistency which is very easily filtered is produced. Under these conditions, crystallisation typically commences after around 1 hour and is typically completed within a few hours (eg 2 hours). Without being limited by theory we believe that this granular product contains little or no of solvated solvent within the crystal lattice.

Step (b) will typically comprise the addition of a reagent suitable for converting the carboxylic acid (III, X=O) into the carbothioic acid (III, X=S) eg. using hydrogen sulphide gas together with a suitable coupling agent eg. carbonyldiimidazole (CDI) in the presence of a suitable solvent eg. dimethylformamide.

Solvates of compounds of formula (I) which are not physiologically acceptable may be useful as intermediates in the preparation of compounds of formula (I) or physiologically acceptable solvates thereof.

Compounds of formula (I) and/or salts or solvates thereof demonstrate agonism at the glucocorticoid receptor.

Compounds of formula (I) and/or salts or solvates thereof may demonstrate good anti-inflammatory properties, with predictable pharmacokinetic and pharmacodynamic behaviour. They also may have an attractive side-effect profile, demonstrated, for example, by increased selectivity for the glucocorticoid receptor over the progesterone receptor and/or increased selectivity for glucocorticoid receptor mediated transrepression over transactivation and are likely to becompatible with a convenient regime of treatment in human patients.

The following non-limiting Examples illustrate the invention:

EXAMPLES

General

Chromatographic purification was performed using prepacked Bond Elut silica gel cartridges available commercially from Varian or by flash chromatography on pre-packed Biotage silica columns. These cartridges were pre-conditioned with dichloromethane prior to use. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. The mass spectra were recorded on a Fisons VG Platform spectrometer using electrospray positive and negative mode (ES+ve and ES−ve). $^1H$ NMR spectra were obtained in $CDCl_3$ on a Bruker DPX 400 spectrometer working at 400.13 MHz and 9.4 Tesla using as internal standard the signal from the residual protonated solvent at 7.25 ppm.

Intermediates

Intermediate 1: 6α,9α-Difluoro-11β-hydroxy-16α-methyl-3-oxo-17α-(2,2,3,3-tetramethycyclopropyl-carbonyl)oxy-androsta-1,4-diene-17-carbothioic Acid Oxalyl chloride (3 ml, 34.9 mmol) was added to a stirred and cooled (ice) solution of 2,2,3,3-tetramethylcyclopropyl carboxylic acid (2.48 g, 17.45 mmol) in dry dichloromethane (70 ml) containing diethylformamide (2 drops) and the mixture stirred for 3 h. The solvent was evaporated and residual acid chloride was redissolved in dichloromethane (15 ml) and added to a stirred and cooled (ice) solution of 6α,9α-difluoro-11β,17α-dihydroxy-16α-methyl-3-oxo-androsta-1,4-diene-17β-carbothioic acid (G. H. Phillipps et al., (1994) Journal of Medicinal Chemistry, 37, 3717-3729) (3 g, 7.27 mmol) in dichloromethane (120 ml) containing triethylamine (2.03 ml, 14.5 mmol). The mixture was allowed to warm to room temperature and after 1.5 h was washed successively with aqueous sodium bicarbonate (150 ml), 1M hydrochloric acid (150 ml) and brine (150 ml) and dried through a hydrophobic frit and evaporated. The residual solid was dissolved in dioxane (140 ml) and 1-methylpiperazine (3.23 ml, 29.1 mmol) was added and the mixture stirred for 4 h. The mixture was then added slowly to a vigorously stirred mixture of 2M hydrochloric acid (200 ml) and ice (200 ml). The mixture was extracted with dichloromethane (300 ml) and the extract washed with water and dried through a hydrophobic frit and evaporated. This material was dissolved in dioxane (80 ml) and treated again with 1-methylpiperazine (3.23 ml) for 20 h. The mixture was added slowly to a vigorously stirred mixture of 2M hydrochloric acid (200 ml) and ice (200 ml). The mixture was extracted with dichloromethane (300 ml) and the extract washed with water and dried through a hydrophobic frit and evaporated. Purification by chromatography on a 90 g biotage cartridge using initially cyclohexane and finally cyclohexane:ethyl acetate (3:1) yielded the title compound (1.33 g): LCMS retention time 3.99 min.

Intermediate 2: 17α-(4-[(Diethylamino)sulphonyl]benzoyl)oxy-6α,9α-difluoro-11β-hydroxy-16α-methyl-3-oxo-androsta-1,4-diene-17β-carbothioic Acid 4-[(Diethylamino)sulphonyl]benzoyl chloride (134 mg) was added to a stirred solution of 6α,9α-difluoro-11β,17α-dihydroxy-16α-methyl-3-oxo-androsta-1,4-diene-17β-carbothioic acid (200 mg) in pyridine (8 ml) and the mixture stirred under nitrogen for 2 h. More acid chloride (134 mg) was the mixture stirred for a further 2 h. 6 M HCl (60 ml) was then added and the mixture extracted with ethyl acetate (3×30 ml). The combined organic extracts were washed with 2M HCl (30 ml), dried through a hydrophobic frit and evaporated to give the title compound as a white foam: LCMS retention time 4.26 min.

Intermediate 3: 17α-(5-Chloro-4-methoxy-thiophene-3-carbonyl)oxy-6α,9α-difluoro-11β-hydroxy-16α-methyl-3-oxo-androsta-1,4-diene-17β-carbothioic Acid Prepared using methods similar to that described for Intermediate 2. LCMS retention time 4.06 min.

Intermediate 4: 6α,9α-Difluoro-11β-hydroxy-16α-methyl-3-oxo-17α-(2,2,3,3-tetramethycyclopropyl-carbonyl)oxy-androsta-1,4-diene-17α-carboxylic Acid Prepared from 6α,9α-difluoro-11β,17α-dihydroxy-16α-methyl-3-oxo-androsta-1,4-diene-17β-carboxylic acid (G. H. Phillipps et al., (1994) Journal of Medicinal Chemistry, 37, 3717-3729) using methods similar to that described for Intermediate 1. LCMS retention time 3.59 min.

Intermediate 5: 17α-(Cyclohexylcarbonyl)oxy-6α,9α-difluoro-11β-hydroxy-16α-methyl-3-oxo-androsta-1,4-diene-17β-carboxylic Acid Cyclohexanecarbonyl chloride (0.081 ml, 0.6 mmol) was added to a stirred and cooled (ice) solution of 6α,9α-difluoro-11β,17α-dihydroxy-16α-methyl-3-oxo-androsta-1,4-diene-17β-carboxylic acid (200 mg, 0.5 mmol) in pyridine (3 ml) and the mixture stirred for 2 h and then poured into 2 M HCl. The mixture was extracted twice with ethyl acetate and the combined organic extracts were washed successively with 2 M HCl and brine and evaporated to give the title compound (296 mg): LCMS retention time 3.67 min.

Intermediate 6: 6α,9α-Difluoro-17α-(2,6-difluorobenzoyl)oxy-11β-hydroxy-16α-methyl-3-oxo-androsta-1,4-diene-17β-carboxylic Acid Prepared using methods similar to that described for Intermediate 5. LCMS retention time 3.45 min.

Intermediate 7: 6α,9α-Difluoro-11β-hydroxy-17α-(4-methoxybenzoyl)oxy-16α-methyl-3-oxo-androsta-1,4-diene-17β-carboxylic Acid Prepared using methods similar to that described for Intermediate 5. LCMS retention time 3.38 min.

Intermediate 8: 17α-(4-Cyanobenzoyl)oxy-6α,9α-difluoro-11β-hydroxy-16α-methyl-3-oxo-androsta-1,4-diene-17β-carboxylic Acid Prepared using methods similar to that described for Intermediate 5. LCMS retention time 3.36 min.

Intermediate 9: 17α-(Cyclopentylmethylcarbonyl)oxy-6α,9α-difluoro-11β-hydroxy-16α-methyl-3-oxo-androsta-1,4-diene-17β-carboxylic Acid Prepared using methods similar to that described for Intermediate 5. LCMS retention time 3.65 min.

Intermediate 10: 6α,9α-Difluoro-17α-(3,3-dimethylbutanoyl)oxy-11β-hydroxy-16α-methyl-3-oxo-androsta-1,4-diene-17β-carboxylic Acid Prepared using methods similar to that described for Intermediate 5. LCMS retention time 3.46 min.

Intermediate 11: 6α,9α-Difluoro-11β-hydroxy-17α-(2-isopropyl-1,3-thiazole-4-carbonyl)oxy-16α-methyl-3-oxo-androsta-1,4-diene-17β-carboxylic Acid Prepared using methods similar to that described for Intermediate 5. LCMS retention time 3.38 min.

Intermediate 12: 6α,9α-Difluoro-11β-hydroxy-16α-methyl-3-oxo-17α-(quinoline-2-carbonyl)oxy-androsta-1,4-diene-17β-carboxylic Acid Prepared using methods similar to that described for Intermediate 5. LCMS retention time 3.46 min.

Intermediate 13: 6α,9α-Difluoro-11β-hydroxy-16α-methyl-3-oxo-17α(5-trifluoromethyl-furan-2-carbonyl)oxy-androsta-1,4-diene-17β-carboxylic Acid Prepared using methods similar to that described for Intermediate 5. LCMS retention time 3.61 min.

Intermediate 14: 6α,9α-Difluoro-11β-hydroxy-16α-methyl-17α-(5-methylsulphonyl-thiophene-2-carbonyl)oxy-3-oxo-androsta-1,4-diene-17β-carboxylic Acid Prepared using methods similar to that described for Intermediate 5. LCMS retention time 3.28 min.

Intermediate 15: 6α,9α-Difluoro-11β-hydroxy-16α-methyl-17α-(5-methylthio-thiophene-2-carbonyl)oxy-3-oxo-androsta-1,4-diene-17β-carboxylic Acid Prepared using methods similar to that described for Intermediate 5. LCMS retention time 3.69 min.

Intermediate 16: 6α,9α-Difluoro-17α-(5-ethyl-isoxazole-3-carbonyl)oxy-11β-hydroxy-16α-methyl-3-oxo-androsta-1,4-diene-17β-carboxylic Acid Prepared using methods similar to that described for Intermediate 5. LCMS retention time 3.45 min.

Intermediate 17: 9α-Fluoro-11β-hydroxy-16β-methyl-3-oxo-17α-(2,2,3,3-tetramethylcyclopropylcarbonyl)oxy-androsta-1,4-diene-17β-carboxylic Acid Prepared from 11β,17α-dihydroxy-9α-fluoro-16β-methyl-3-oxo-androsta-1,4-diene-17β-carboxylic acid (G. H. Phillipps et al., (1994) Journal of Medicinal Chemistry, 37, 3717-3729) and 2,2,3,3-tetramethylcyclopropyl carbonyl chloride using methods similar to that described for Intermediate 5. LCMS retention time 3.75 min.

Intermediate 18: 17α-(5-Chloro-4-methoxy-thiophene-3-carbonyl)oxy-6α,9α-difluoro-11β-hydroxy-16α-methyl-3-oxo-androsta-1,4-diene-17b-carboxylic Acid Prepared using methods similar to that described for Intermediate 5. LCMS retention time 3.59 min.

Intermediate 19: 17α-(2,2-Dichloro-3,3-dimethylclopropylcarbonyl)oxy-6α,9α-difluoro-11β-hydroxy-16α-methyl-3-oxo-androsta-1,4-diene-17β-carboxylic Acid Prepared using methods similar to that described for Intermediate 1. LCMS retention time 3.58 min.

Intermediate 20: 17α-(2,2-Dichloro-3,3-dimethylclopropylcarbonyl)oxy-6α,9α-difluoro-11β-hydroxy-16α-methyl-3-oxo-androsta-1,4-diene-17-carbothioic Acid Prepared using methods similar to that described for Intermediate 1. LCMS retention time 4.10, 4.19 min.

Intermediate 21: 17α-(Cyclohexylcarbonyl)oxy-6α,9α-difluoro-11β-hydroxy-16α-methyl-3-oxo-androsta-1,4-diene-17β-carbothioic Acid Prepared using methods similar to that described for Intermediate 1. LCMS retention time 4.17 min.

Intermediate 22: 6α,9α-Difluoro-11β-hydroxy-16α-methyl-17α-(5-methylsulphonyl-thiophene-2-carbonyl)oxy-3-oxo-androsta-1,4-diene-17β-carbothioic Acid Prepared using methods similar to that described for Intermediate 1. LCMS retention time 4.10 min.

Intermediate 23: 6α,9α-Difluoro-11β-hydroxy-16α-methyl-3-oxo-17α-(5-trifluoromethyl-furan-2-carbonyl)oxy-androsta-1,4-diene-17β-carbothioic Acid Prepared using methods similar to that described for Intermediate 1. LCMS retention time 4.45 min.

Intermediate 24: 6α,9α-Difluoro-17α-(3-(difluoromethylthio)benzoyl)oxy-11β-hydroxy-16α-methyl-3-oxo-androsta-1,4-diene-17β-carbothioic Acid Prepared using methods similar to that described for Intermediate 1. LCMS retention time 4.23 min.

Intermediate 25: 2,3-dimethyl-1-[(2,2,3,3-tetramethylcyclopropyl)carbonyl]-1H-imidazol-3-ium Chloride Oxalyl chloride (360 ml, 4.1 mol) was added over 65 min to a stirred solution of 2,2,3,3-tetramethylcyclopropane carboxylic acid (600 g, 4.2 mol) in dichloromethane (3.6 L) at 34° C. The solution was then heated to reflux for 30 min and then cooled to 5° C. A solution of 1,2-dimethylimidazole (490 g, 5.1 mol) in dichloromethane (1.2 L) was added over 45 min maintaining the internal temperature around 5° C. The resulting suspension was then warmed to 18° C. and acetone (4.8 L) was added over 45 minutes maintaining the internal temperature around 18° C. The slurry was cooled to 5° C. over 30 minutes, stirred at 5° C. for 30 minutes and then filtered. The product was collected by filtration, washed with acetone:dichloromethane (3:1, 3×1.2 L), sucked dry and then dried in a vacuum oven at 25-30° C. for 10 hours to give Intermediate 25 as a white solid (890 g) 1H nmr: $\delta_H$ (CDCl$_3$, 400 MHz) 8.45 (d, J=2.4 Hz, 1H), 8.11 (d, J=2.4 Hz, 1H), 4.21 (s, 3H), 2.96 (s, 3H), 2.21 (s, 1H), 1.43 (s, 6H), 1.33 (s, 6H).

EXAMPLES

Example 1

6α,9α-Difluoro-11β-hydroxy-16α-methyl-3-oxo-17α-(2,2,3,3-tetramethycyclopropylcarbonyl)oxy-androsta-1,4-diene-17β-carbothioic Acid S-cyanomethyl Ester Bromoacetonitrile (0.042 ml, 0.6 mmol) was added to a stirred and cooled (ice) solution of Intermediate 1 (120 mg, 0.22 mmol) and sodium hydrogen carbonate (21 mg, 0.245 mmol) in DMF (3 ml) under nitrogen and the mixture stirred at room temperature for 18 h. Diethylamine (0.03 ml, 0.29 mmol) was added and the mixture stirred for 15 min when 2M HCl (4 ml) and then water (5 ml) and dichloromethane (5 ml) were added. The organic phase was separated washed successively with aqueous sodium hydrogen carbonate (5 ml) and brine (5 ml) and dried through a hydrophobic frit and evaporated to dryness. Purification on a Bon Elut cartridge using initially cyclohexane and finally cyclohexane:ethyl acetate 3:1 gave the title compound (86 mg): LCMS retention time 3.82 min, m/z 576 MH$^+$

Example 2

17α-(4-[(Diethylamino)sulphonyl]benzoyl)oxy-6α,9α-difluoro-11β-hydroxy-16α-methyl-3-oxo-androsta-1,4-diene-17β-carbothioic Acid S-cyanomethyl Ester Example 2 was prepared from Intermediate 2 using a method similar to that described for Example 1. LCMS retention time 3.62 min, m/z 691 MH$^+$

Example 3

17α-(5-Chloro-4-methoxy-thiophene-3-carbonyl)oxy-6α,9α-difluoro-11β-hydroxy-16α-methyl-3-oxo-androsta-1,4-diene-17β-carbothioic Acid S-cyanomethyl Ester Example 3 was prepared from Intermediate 3 using a method similar to that described for Example 1. LCMS retention time 3.58 min, m/z 626/628 MH$^+$

Example 4

6α,9α-Difluoro-11β-hydroxy-16α-methyl-3-oxo-17α-(2,2,3,3-tetramethycyclopropylcarbonyl)oxy-androsta-1,4-diene-17β-carboxylic Acid cyanomethyl Ester Method A Bromoacetonitrile (0.229 ml, 3.29 mmol) was added to a stirred and cooled (ice) solution of Intermediate 4 (634 mg, 1.22 mmol) and sodium carbonate (1.29 g, 12.2 mmol) in DMF (15 ml) under nitrogen and the mixture stirred at room temperature for 2 h. More sodium carbonate (258 mg) was added and the mixture stirred for a further 18 h. 2M HCl (20 ml) was added dropwise followed by water (25 ml) and the mixture was extracted with ethyl acetate (2×50 ml). The combined organic extracts were washed successively with aqueous sodium hydrogen carbonate (50 ml) and brine (50 ml) and dried through a hydrophobic frit and evaporated to dryness. Purification on a Bon Elut cartridge using initially cyclohexane and finally cyclohexane:ethyl acetate 3:1 gave the title compound as a white solid (485 mg): LCMS retention time 3.79 min, m/z 560 MH$^+$ Method B 6α,9α-Difluoro-11β,17α-dihydroxy-16α-methyl-3-oxo-androsta-1,4-diene-17β-carboxylic acid (490 g, 1.2 mol) and Intermediate 25 (790 g, 3.1 mol) were suspended in 3-pentanone (7.3 L). To the stirred suspension was added over 10 min a solution of 1,2-dimethylimidazole (120 g, 1.2 mol) in water (730 ml) maintaining the internal temperature around 19° C. After 35 min, 1-methylpiperazine (230 ml, 2.1 mol) was added over 10 min keeping the internal temperature around 19° C. The mixture was stirred for 30 min and then washed sequentially with 2M HCl (290 ml) and water (290 ml). Diisopropylethylamine (430 ml, 2.5 mol) and bromoacetonitrile (120 ml, 1.7 mol) were added sequentially to the solution and the mixture was heated to 53° C. for 13 hours. The solution was cooled to 34° C. and 1-methylpiperazine (105 ml) was added. The mixture was stirred around 34° C. for a further hour, cooled to 25° C. and washed sequentially with 2M HCl (290 ml), water (290 ml), 2% potassium carbonate solution (290 ml) and water (290 ml). The organic solution was concentrated to 3.9 L by atmospheric distillation, cooled to 75° C. and seeded with crystals of Example 4.

2,2,4-Trimethylpentane (6.83 L) was added over 3 hours at 75° C. and the slurry was then cooled to 10° C. over 2 hours, stirred for a further 30 min and then filtered. The product was washed with 3-pentanone:2,2,4-trimethylpentane (1:3, 3×1 L), sucked dry and finally dried in a vacuum oven at 50° C. for 12 hours to give Example 4 as a white solid (640 g) identical to material obtained using Method A.

Example 5

17α-(Cyclohexylcarbonyl)oxy-6α,9α-difluoro-11β-hydroxy-16α-methyl-3-oxo-androsta-1,4-diene-17β-carboxylic Acid cyanomethyl Ester Example 5 was prepared from Intermediate 5 using a method similar to that described for Example 4. LCMS retention time 3.65 min, m/z 546 MH$^+$ Example 6

6α,9α-Difluoro-17α-(2,6-difluorobenzoyl)oxy-11β-hydroxy-16α-methyl-3-oxo-androsta-1,4-diene-17β-carboxylic Acid cyanomethyl Ester Example 6 was prepared from Intermediate 6 using a method similar to that described for Example 4. LCMS retention time 3.48 min, m/z 576 MH$^+$ Example 7

6α,9α-Difluoro-11β-hydroxy-17α-(4-methoxybenzoyl)oxy-16α-methyl-3-oxo-androsta-1,4-diene-17β-carboxylic Acid cyanomethyl Ester Example 7 was prepared from Intermediate 7 using a method similar to that described for Example 4. LCMS retention time 3.53 min, m/z 570 MH$^+$ Example 8

17α-(4-Cyanobenzoyl)oxy-6α,9α-difluoro-11β-hydroxy-16α-methyl-3-oxo-androsta-1,4-diene-17β-carboxylic Acid Cyanomethyl Ester Example 8 was prepared from Intermediate 8 using a method similar to that described for Example 4. LCMS retention time 3.44 min, m/z 565 MH$^+$ Example 9

17α-(Cyclopentylmethylcarbonyl)oxy-6α,9α-difluoro-11β-hydroxy-16α-methyl-3-oxo-androsta-1,4-diene-17β-carboxylic Acid Cyanomethyl Ester Example 9 was prepared from Intermediate 9 using a method similar to that described for Example 4. LCMS retention time 3.69 min, m/z 546 MH$^+$ Example 10

6α,9α-Difluoro-17α-(3,3-dimethylbutanoyl)oxy-11β-hydroxy-16α-methyl-3-oxo-androsta-1,4-diene-17β-carboxylic Acid Cyanomethyl Ester Example 10 was prepared from Intermediate 10 using a method similar to that described for Example 4. LCMS retention time 3.60 min, m/z 534 MH$^+$ Example 11

6α,9α-Difluoro-11β-hydroxy-17α-(2-isopropyl-1,3-thiazole-4-carbonyl)oxy-16α-methyl-3-oxo-androsta-1,4-diene-17β-carboxylic Acid Cyanomethyl Ester Example 11 was prepared from Intermediate 11 using a method similar to that described for Example 4. LCMS retention time 3.50 min, m/z 589 MH$^+$ Example 12

6α,9α-Difluoro-11β-hydroxy-16α-methyl-3-oxo-17α-(quinoline-2-carbonyl)oxy-androsta-1,4-diene-17β-carboxylic Acid Cyanomethyl Ester Example 12 was prepared from Intermediate 12 using a method similar to that described for Example 4. LCMS retention time 3.61 min, m/z 591 MH$^+$ Example 13

6α,9α-Difluoro-11β-hydroxy-16α-methyl-3-oxo-17α-(5-trifluoromethyl-furan-2-carbonyl)oxy-androsta-1,4-diene-17β-carboxylic Acid Cyanomethyl Ester Example 13 was prepared from Intermediate 13 using a method similar to that described for Example 4. LCMS retention time 3.72 min, m/z 598 MH$^+$ Example 14

6α,9α-Difluoro-11β-hydroxy-16α-methyl-17α-(5-methylsulphonyl-thiophene-2-carbonyl)oxy-3-oxo-androsta-1,4-diene-17β-carboxylic Acid Cyanomethyl Ester Example 14 was prepared from Intermediate 14 using a method similar to that described for Example 4. LCMS retention time 3.29 min, m/z 624 MH$^+$ Example 15

6α,9α-Difluoro-11β-hydroxy-16α-methyl-17α-(5-methylthio-thiophene-2-carbonyl)oxy-3-oxo-androsta-1,4-diene-17β-carboxylic Acid Cyanomethyl Ester Example 15 was prepared from Intermediate 15 using a method similar to that described for Example 4. LCMS retention time 3.64 min, m/z 592 MH$^+$ Example 16

6α,9α-Difluoro-17α-(5-ethyl-isoxazole-3-carbonyl)oxy-11β-hydroxy-16α-methyl-3-oxo-androsta-1,4-diene-17β-carboxylic Acid Cyanomethyl Ester Example 16 was prepared from Intermediate 16 using a method similar to that described for Example 4. LCMS retention time 3.44 min, m/z 559 MH$^+$

Example 17

9α-Fluoro-11β-hydroxy-16β-methyl-3-oxo-17α-(2,2,3,3-tetramethylcyclopropylcarbonyl)oxy-androsta-1,4-diene-17 b-carboxylic Acid cyanomethyl ester Example 17 was prepared from Intermediate 17 using a method similar to that described for Example 4. LCMS retention time 3.77 min, m/z 542 MH$^+$

Example 18

6α,9α-Difluoro-11β-hydroxy-16α-methyl-3-oxo-17α-(2,2,3,3-tetramethycyclopropylcarbonyl)oxy-androst-4-ene-17 b-carboxylic Acid Cyanomethyl Ester A solution of Example 4 (1.8 g, 3.2 mmol) and Wilkinson's catalyst (0.5 g, 0.54 mmol) in a 2:1 mixture of toluene and ethyl acetate (130 ml) was hydrogenated for 5 days. A further batch of catalyst (0.5 g) was added after 1 day. The solution was evaporated and the residue was chromatographed on a 100 g silicia cartridge using firstly a cyclohexane:ethyl acetate 0-30% gradient over 15 min and then cyclohexane:ethyl acetate 30% for 10 min. Appropriate fractions were combined and evaporated to give title compound as a white solid (400 mg): LCMS retention time 3.73 min, m/z 579 MNH$_4^{+-}$.

Example 19

17α-(5-Chloro-4-methoxy-thiophene-3-carbonyl)oxy-6α,9α-difluoro-11β-hydroxy-16α-methyl-3-oxo-androsta-1,4-diene-17β-carboxylic Acid Cyanomethyl Ester Example 19 was prepared from Intermediate 18 using a method similar to that described for Example 4. LCMS retention time 3.57 min, m/z 610, 612 MH$^+$

Example 20

17α-(2,2-Dichloro-3,3-dimethylclopropylcarbonyl)oxy-6α,9α-difluoro-11β-hydroxy-16α-methyl-3-oxo-androsta-1,4-diene-17β-carboxylic Acid Cyanomethyl Ester Example 20 was prepared from Intermediate 19 using a method similar to that described for Example 4. LCMS retention time 3.62 min, m/z 600, 602, 604 MH$^+$

Example 21

17α-(22-Dichloro-3,3-dimethylclopropylcarbonyl)oxy-6α,9α-difluoro-11β-hydroxy-16α-methyl-3-oxo-androsta-1,4-diene-17β-carbothioic acid S-cyanomethyl Ester Example 21 was prepared from Intermediate 20 using a method similar to that described for Example 1. LCMS retention time 3.58 min, m/z 616, 618, 620 MH$^+$

Example 22

17α-(Cyclohexylcarbonyl)oxy-6α,9α-difluoro-1,1-hydroxy-16α-methyl-3-oxo-androsta-1,4-diene-17β-carbothioic Acid S-cyanomethyl Ester Example 22 was prepared from Intermediate 21 using a method similar to that described for Example 1. LCMS retention time 3.60 min, m/z 562 MH$^+$

Example 23

6α,9α-Difluoro-11β-hydroxy-16α-methyl-17α-(5-methylsulphonyl-thiophene-2-carbonyl)oxy-3-oxo-androsta-1,4-diene-17β-carbothioic Acid S-cyanomethyl Ester Example 23 was prepared from Intermediate 22 using a method similar to that described for Example 1. LCMS retention time 3.30 min, m/z 640 MH$^+$

Example 24

6α,9α-Difluoro-11β-hydroxy-16α-methyl-3-oxo-17α-(5-trifluoromethyl-furan-2-carbonyl)oxy-androsta-1,4-diene-17β-carbothioic Acid S-cyanomethyl Ester Example 24 was prepared from Intermediate 23 using a method similar to that described for Example 1. LCMS retention time 3.60 min, m/z 614 MH$^+$

Example 25

6α,9α-Difluoro-17α-(3-(difluoromethylthio)benzoyl)oxy-11β-hydroxy-16α-methyl-3-oxo-androsta-1,4-diene-17β-carbothioic Acid S-cyanomethyl Ester Example 25 was prepared from Intermediate 24 using a method similar to that described for Example 1. LCMS retention time 3.65 min, m/z 638 MH$^+$ Pharmacological Activity Pharmacological activity may be assessed in functional in vitro assays of glucocorticoid agonist activity.

The functional assay based on that described by K. P. Ray et al., Biochem J. (1997), 328, 707-715 provides a measure of transrepressive activity of a glucocorticoid agonist. A549 cells stably transfected with a reporter gene containing the NF-κB responsive elements from the ELAM gene promoter coupled to sPAP (secreted alkaline phosphatase) are treated with test compounds at appropriate doses for 1 hour at 37° C. The cells are then stimulated with tumour necrosis factor (TNF, 10 ng/ml) for 16 hours, at which time the amount of alkaline phosphatase produced is measured by a standard colourimetric assay. Dose response curves are constructed from which EC$_{50}$ values may be estimated.

The EC$_{50}$ values for compounds of Examples 1 to 25 were <10 nM.

EC$_{50}$ values of <1 nM were observed for Examples 1 to 11, 14 to 22 and 25

EC$_{50}$ values of ≦0.1 nM were observed for Examples 4, 8, 15 and 20

The functional assay based on that described by R. J. H. Austin et al., Eur Resp J. (2002), 20, 1386-1392 measures the ability of compounds to directly transactivate gene expression. A549 cells stably transfected with a reporter gene containing the glucocorticoid responsive region of the mouse mammary tumour virus long terminal repeat (MMTV-LTR) coupled to renilla luciferase were treated with test com pounds at appropriate doses for 6 hour at 37° C. The amount of luciferase activity present within the cells is then determined by measuring the light emitted following incubation with a suitable substrate. Dose response curves were constructed from which $EC_{50}$ values were estimated and from which maximal responses are calculated relative to Dexamethasone (100%).

Compounds of Examples 1 to 25 showed maximal responses of <35% in this assay.

Compounds of Examples 1, 2, 4, 5, 6, 9 to 11, 13 and 15 to 25 showed maximal responses of <20% in this assay.

Compounds of Examples 2 and 4 showed maximal responses of <5% in this assay.

Assay for Progesterone Receptor Activity

The human breast cancer cell line T47D has been reported to upregulate an endogenous alkaline phosphatase in response to progestins (Di Lorenzo et al., Cancer Research (1991) 51, 4470-4475. T47D cells were seeded into 96 well plates at a density of $1\times10^5$ cells per well and grown overnight at 37° C. Steroids were dissolved in DMSO, added to the cells (final DMSO concentration 0.7%), and incubated for 24 hours at 37° C. The cells were then washed with PBS and lysed with RIPA buffer (1% IGEPAL, 0.5% Na deoxycholate, 0.1% SDS in phosphate buffered saline). Alkaline phosphatase activity was measured spectrophotometrically (405 nm) using p-nitrophenylphosphate (1.5 mg/ml) as a substrate dissolved in 1 M diethanolamine, 0.28M NaCl, 0.5 mM $MgCl_2$. Dose response curves were constructed from which $EC_{50}$ values were estimated.

The $EC_{50}$ values for compounds of Examples 4, 5, 8, 11, 18, 20, 23, 24 and 25 in this assay were >100 nM Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

The invention claimed is:

1. A pharmaceutical composition comprising:
a) a compound of formula (I):

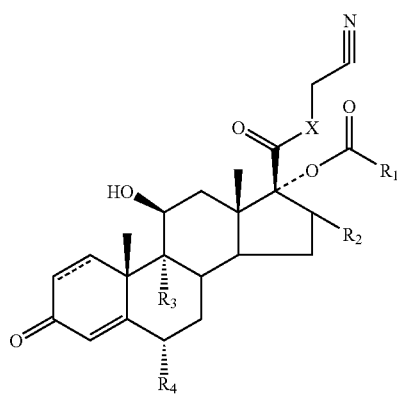

(I)

wherein
X represents O or S;
$R_1$ represents $C_{1-6}$ alkyl, $C_{3-8}$ cycloalkyl, $C_{3-8}$ cycloalkylmethyl or $C_{3-8}$ cycloalkenyl any of which optionally may be substituted by one or more methyl groups or halogen atoms or
$R_1$ represents aryl, substituted aryl, heteroaryl or substituted heteroaryl;
$R_2$ represents hydrogen, methyl, which may be in either the α or β configuration, or methylene;
$R_3$ and $R_4$ are the same or different and each independently represents hydrogen, halogen or a methyl group;
and ═══ represents a single or a double bond;
or a physiologically acceptable salt thereof, and
(b) a diluent or carrier, and
wherein the compound of formula (I) or a physiologically acceptable salt thereof comprises from 0.0001 to 10% by weight of said pharmaceutical composition.

2. A pharmaceutical composition of claim 1, wherein in the compound of formula (I) or a physiologically acceptable salt thereof, X represents O.

3. A pharmaceutical composition of claim 2, wherein, in the compound of formula (I) or a physiologically acceptable salt thereof, $R_1$ represents a $C_{3-6}$ cycloalkyl group optionally substituted by one or more methyl or chlorine groups.

4. A pharmaceutical composition of claim 3, wherein, in the compound of formula (I) or a physiologically acceptable salt thereof, $R_1$ represents 2,2,3,3-tetramethylcyclopropyl.

5. A pharmaceutical composition of claim 4, wherein, in the compound of formula (I) or a physiologically acceptable salt thereof, $R_2$ represents methyl in the α-configuration.

6. A pharmaceutical composition of claim 5, wherein, in the compound of formula (I) or a physiologically acceptable salt thereof, $R_3$ and $R_4$ are both fluorine.

7. A pharmaceutical composition of claim 6, wherein, in the compound of formula (I) or a physiologically acceptable salt thereof, ═══ represents a double bond.

8. The pharmaceutical composition of claim 1, wherein the compound of formula (I) or a physiologically acceptable salt thereof comprises from 0.005 to 1% by weight of said pharmaceutical composition.

9. The pharmaceutical composition of claim 1, wherein the compound of formula (I) or a physiologically acceptable salt thereof comprises 0.01 to 0.5% by weight of said pharmaceutical composition.

10. The pharmaceutical composition of claim 1, wherein the diluent or carrier is suitable for inhalation, and wherein the at least one pharmaceutically active compound comprises from 0.1 to 5% by weight of the pharmaceutical composition.

11. A pharmaceutical formulation of claim 10, comprising a fluorocarbon or hydrogen-containing chlorofluoro carbon as propellant, optionally in combination with a surfactant and/or a cosolvent.

12. A pharmaceutical composition according to claim 9, which further comprises one or more other therapeutic agents, selected from the group consisting of anti-inflammatory agents, anticholinergic agents, β-adrenoreceptor agonists, antiinfective agents and antihistamines, and combinations thereof.

13. A pharmaceutical composition of claim 1, wherein, in the compound of formula (I) or a physiologically acceptable salt thereof:
X represents O;
$R_1$ represents a $C_{3-6}$ cycloalkyl group optionally substituted by one or more methyl groups;
$R_2$ represents methyl in the α-configuration;
$R_3$ and $R_4$ are both fluorine; and
═══ represents a double bond.

14. A method for the treatment of a human or animal subject with an inflammatory and/or allergic condition, which method comprises administering to said human or animal subject an effective amount of a pharmaceutical composition comprising:
   a) a compound of formula (I):

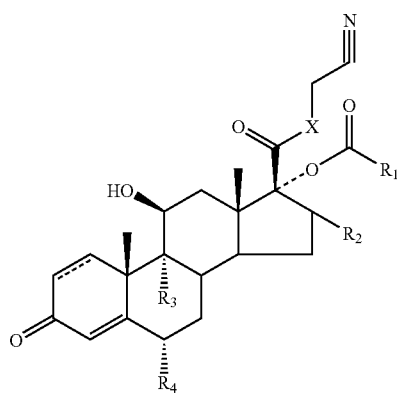

wherein
   X represents O or S;
   $R_1$ represents $C_{1-6}$ alkyl, $C_{3-8}$ cycloalkyl, $C_{3-8}$ cycloalkylmethyl or $C_{3-8}$ cycloalkenyl any of which optionally may be substituted by one or more methyl groups or halogen atoms or
   $R_1$ represents aryl, substituted aryl, heteroaryl or substituted heteroaryl;
   $R_2$ represents hydrogen, methyl, which may be in either the α or β configuration, or methylene;
   $R_3$ and $R_4$ are the same or different and each independently represents hydrogen, halogen or a methyl group;
   and ==== represents a single or a double bond;
   or a physiologically acceptable salt thereof, and
   (b) a diluent or carrier, and
      wherein the compound of formula (I) or a salt thereof comprises from 0.0001 to 10% by weight of said pharmaceutical composition.

15. The method of claim 14, wherein said effective amount of said pharmaceutical composition contains from 20 to 2000 micrograms of the compound of formula (I) or a physiologically acceptable salt thereof.

16. The method of claim 15, wherein said effective amount of said pharmaceutical composition contains from 20 to 500 micrograms of a compound of formula (I) or a physiologically acceptable salt thereof.

17. The method of claim 14, wherein said effective amount of said pharmaceutical composition is delivered at least once per day.

18. The method of claim 17, wherein said effective amount of said pharmaceutical composition is delivered once per day.

19. The method of claim 14, wherein the inflammatory and/or allergic condition is selected from the group consisting asthma and rhinitis.

20. The method of claim 14, wherein the inflammatory and/or allergic condition effects the conjunctiva.

21. A pharmaceutical composition comprising:
   a) a compound of formula (I):

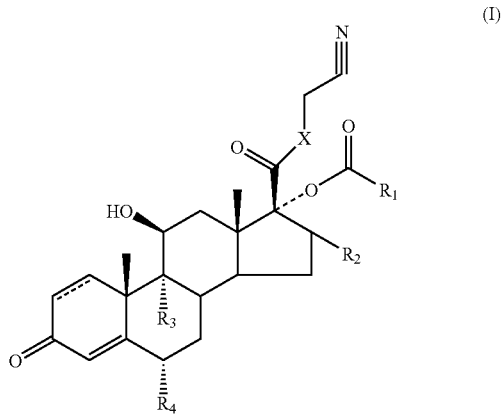

wherein
   X represents O or S;
   $R_1$ represents $C_{1-6}$ alkyl, $C_{3-8}$ cycloalkyl, $C_{3-8}$ cycloalkylmethyl or $C_{3-8}$ cycloalkenyl any of which optionally may be substituted by one or more methyl groups or halogen atoms or
   $R_1$ represents aryl, substituted aryl, heteroaryl or substituted heteroaryl;
   $R_2$ represents hydrogen, methyl, which may be in either the α or β configuration, or methylene;
   $R_3$ and $R_4$ are the same or different and each independently represents hydrogen, halogen or a methyl group;
   and ==== represents a single or a double bond;
or a physiologically acceptable salt thereof;
   (b) a diluent or carrier suitable for inhalation or insufflation; and
   (c) another therapeutically active agent,
      wherein the compound of formula (I) or a physiologically acceptable salt thereof comprises from 0.0001 to 10% by weight of said pharmaceutical composition.

22. A method for the treatment of a human or animal subject with an inflammatory and/or allergic condition, which method comprises administering to said human or animal subject an effective amount of the pharmaceutical composition of claim 21.

23. The method of claim 22, wherein said effective amount of said pharmaceutical composition contains from 20 to 2000 micrograms of the compound of formula (I) or a physiologically acceptable salt thereof.

24. The method of claim 23, wherein said effective amount of said pharmaceutical composition is delivered once or twice per day.

25. The method of claim 24, wherein said effective amount of said pharmaceutical composition is delivered once per day.

* * * * *